(12) United States Patent
Janson et al.

(10) Patent No.: US 12,285,629 B2
(45) Date of Patent: Apr. 29, 2025

(54) ROBUST TREATMENT PLANNING OR PLAN EVALUATION

(71) Applicant: RaySearch Laboratories AB (Publ), Stockholm (SE)

(72) Inventors: Martin Janson, Enskededalen (SE); Agnes Angerud, Jarfalla (SE)

(73) Assignee: Raysearch Laboratories AB (publ), Stockholm (SE)

( * ) Notice: Subject to any disclaimer, the term of this patent is extended or adjusted under 35 U.S.C. 154(b) by 160 days.

(21) Appl. No.: 18/005,674

(22) PCT Filed: Jun. 14, 2021

(86) PCT No.: PCT/EP2021/065960
§ 371 (c)(1),
(2) Date: Jan. 17, 2023

(87) PCT Pub. No.: WO2022/017684
PCT Pub. Date: Jan. 27, 2022

(65) Prior Publication Data
US 2023/0285775 A1 Sep. 14, 2023

(30) Foreign Application Priority Data

Jul. 20, 2020 (EP) ...................................... 20186651

(51) Int. Cl.
*A61N 5/10* (2006.01)
*G16H 20/40* (2018.01)
(52) U.S. Cl.
CPC ........... *A61N 5/1038* (2013.01); *G16H 20/40* (2018.01)
(58) Field of Classification Search
CPC .... A61N 5/1038; A61N 5/1037; A61N 5/103; G16H 20/40
See application file for complete search history.

(56) References Cited

FOREIGN PATENT DOCUMENTS

| EP | 3081262 A1 | 10/2016 |
|----|------------|---------|
| EP | 3108932 A1 | 12/2016 |

(Continued)

OTHER PUBLICATIONS

Van de Water et al., Anatomical robust optimization to deal with variation in nasal cavity filling during IMPT, Radiotherapy and Oncology, vol. 123, Supplement 1, pp. S437-S438.

(Continued)

*Primary Examiner* — Dani Fox
*Assistant Examiner* — Mamadou Faye
(74) *Attorney, Agent, or Firm* — Noréns Patentbyrå AB

(57) ABSTRACT

In cases where material properties of a structure within or outside a patient receiving radiotherapy treatment, robust planning can be used, based on different scenarios with different material property values using a material override function present in the treatment planning system.

A computer-based method of generating a radiotherapy treatment plan for a patient, based on an image of the patient and a desired dose. In cases where material properties of a structure within or outside a patient receiving radiotherapy treatment, robust planning can be used, based on different scenarios with different material property values using a material override function present in the treatment planning system. Robust planning is performed based on the at least two scenarios to provide robust evaluation data for each of the at least two scenarios and/or a robust optimized treatment plan with respect to all values in the set of material override values.

9 Claims, 2 Drawing Sheets

(56) References Cited

FOREIGN PATENT DOCUMENTS

| | | | | |
|---|---|---|---|---|
| EP | 3228356 A1 | * | 10/2017 | ........... A61N 5/1031 |
| EP | 3228357 A1 | * | 10/2017 | ........... A61N 5/1031 |
| EP | 3384961 A1 | | 10/2018 | |
| JP | 2018510664 A | | 4/2018 | |
| JP | 2019510585 A | | 4/2019 | |
| JP | 2019524304 A | | 9/2019 | |
| JP | 2020516360 A | | 6/2020 | |
| JP | 2021530277 A | | 11/2021 | |
| WO | 2016070938 A1 | | 5/2016 | |
| WO | 2020002334 A1 | | 1/2020 | |

OTHER PUBLICATIONS

International Search Report & Written Opinion, European Patent Office, Aug. 24, 2021, Rijswijk, Netherlands.
Office action dated Feb. 18, 2025 in corresponding Japanese patent application No. 2022-571795, Japan Patent Office, Tokyo, Japan.

* cited by examiner

ROBUST TREATMENT PLANNING OR PLAN EVALUATION

TECHNICAL FIELD

The present invention relates to a computer-based method for calculation or evaluation of a radiotherapy treatment plan, in particular for robust treatment planning.

BACKGROUND

Conventional radiotherapy treatment planning involves providing one or more medical images of a patient, determining a desired dose distribution and optimizing a plan that comes as close as possible to the desired dose distribution.

The plan takes into account various factors, such as the patient's geometry, the material properties of different regions of the patient, such as densities, and other factors such as patient movement. It is recognized that the patient's exact position on the treatment couch and internal geometry generally cannot be known exactly. Methods for robust treatment planning are known, taking into account the uncertainties in factors such as the patient's position on the treatment couch, the exact position of tumorous cells, possible anatomical changes to the patient during a treatment fraction or between treatment fractions. A robust treatment plan should be insensitive to any errors occurring due to such uncertainties.

Robust planning methods are known which take uncertainties in position and/or geometry of the patient into account directly in the optimization. The possible realizations of the uncertainties are often discretized into a plurality of scenarios, where each scenario corresponds to a specific realization of the uncertainties. As a simple example, different scenarios can be defined by different rigid translations of the patient, corresponding to different possible setup errors.

For example, WO2016/070938 by the same applicant discloses a method for generating a robust radiotherapy treatment plan with respect to uncertainties that are relevant for treatment planning, including range uncertainties, patient setup uncertainties and organ motion and deformation in patient geometry. For example, different possible positions for a target volume may be included in the planning, and weights may be assigned to voxels depending on how many of the possible positions for the target volume they are included in.

In some cases, there is also an uncertainty in the material properties of a region of the patient. Material properties, such as density, will affect the propagation of the radiation through the patient. For example, with photon radiotherapy, a structure in the beam path having a higher actual density than the one assumed in the planning will lower the dose actually delivered to the target. With proton therapy, a higher or lower actual density will move the position of the Bragg peak, causing the dose to be delivered in a different place. Both these scenarios are undesired.

Situations in which uncertainties in material property may occur include:
- Implants or prosthetic devices where the material is not known. Such devices are typically made from one of a limited number of suitable materials, such as titanium or various biocompatible alloys. Their shape is usually well-defined.
- Other added structures, such as tooth fillings may have undefined shape as well as a wide range of materials.
- Nasal filling, air or mucus. Again, the shape of the nasal cavities is relatively constant, but they may be more or less clogged.
- Colon gas bubble formation
- Breast swelling In some situations, including the latter two, there is also uncertainty in the shape of the structure of unknown material. Attempts have been made to handle uncertainties in patient geometry, such as gas bubble formation, by considering the fraction image for up-to-date information about this, but this will not always provide reliable material property values. Also, even with recent images the air bubbles can move around after the image is taken. Further, in some cases, it is not desirable or feasible to capture new images of the patient on the day of a treatment fraction. For such cases, it may be advantageous to perform robust planning in advance. For implants or prosthetic devices, it is standard practice to select beam angles that avoid these regions. If beams are planned through or close to these regions, normally a suitable set of material properties is chosen and used in the planning procedure, such as the most likely material, or an average value of different possible materials. The dose resulting from the plan may be evaluated and, if necessary, a new plan may be produced using a different set of material values.

Van de Water et al., Anatomical robust optimization to deal with variation in nasal cavity filling during IMPT, Radiotherapy and Oncology, Volume 123, Supplement 1, Pages S437-S438, discusses different ways of handling interfractional variations in the filling of nasal cavities based on a number of artificial CT images. The proposed methods are varying planning target volume margins, anatomical robust optimization or online plan adaptation in which a new treatment plan is generated for each of the artificial images.

SUMMARY OF THE INVENTION

It is an object of the invention to provide more reliable treatment plans in situations where material properties for one or more regions in or around a patient are not known. The regions around the patient may include one or more of a support, fixation, bolus and/or couch.

The invention relates to a computer-based method of generating a radiotherapy treatment plan for a patient, comprising the following steps:
a. obtaining an image of the patient and a desired dose to at least one portion of the patient,
b. identifying at least one structure in the image for which there is an uncertainty in at least one parameter,
c. defining two or more different scenarios for the structure, with respect to the at least one parameter, each scenario including a set of material override values for the structure, the values corresponding to different possible values for the at least one parameter,
d. performing calculations based on the at least two scenarios to provide robust evaluation data for each of the at least two scenarios and/or a robust optimized treatment plan with respect to all values in the set of material override values.

Hence, the invention utilizes the function of the treatment planning system which allows setting the material property values in the image to define different scenarios with different material property values for one or more portion of the image in which there is an uncertainty. The uncertainty may be in the material or material composition used in the area, but it may also relate to uncertainties in the position or shape of the portion.

In some embodiments, the at least one parameter is related to the material properties of the structure and the set of material override values relate to at least one material property of the structure. This is relevant, for example, in the case of implants, where the material of the implant is not known but can be one of a number of known materials. The at least one material property of the structure may include one or more material properties as will be discussed below.

The structure may be an implant or a prosthetic device that has been inserted into the patient's body. It may also be a natural part of the patient's body in which the shape and/or content may vary, such as a bowel, the urine bladder or a nasal cavity. Alternatively, the structure is a structure external of the patient, such as a couch, a chair, a fixation or a bolus, which will also affect the dose delivery.

In some embodiments, the at least one structure is added to the image by changing the material settings in a portion of the image and the parameter is related to the position of the portion of the image, such that the material property value is changed for different portions of the image in different scenarios, the method further comprising the steps of obtaining a definition of the structure.

As is common in robust planning, different weights may be assigned to the different possible values in the calculation procedure depending on the probability of the different possible values.

If the calculation is performed to provide robust evaluation data, the method may further include the step of using the robust evaluation data to evaluate the at least two scenarios. This will provide an assessment of how well the plan will work for each of the different scenarios, for example, to indicate if the plan is clinically acceptable for all scenarios. If the plan is not found to be clinically acceptable for all scenarios, the plan may be discarded.

In some embodiments, the invention is based on providing robust data for optimization or evaluation of a treatment plan, taking into account uncertainties in material properties, shape and/or position by possible material settings in a part of the data. For optimization, this means that possible material property values are considered already in the planning procedure, to produce a plan that will be sufficiently good for all the different scenarios for the unknown structure, including possible material properties and/or possible variations in the structure's position and/or shape. This is done by providing a list of different material properties and/or shapes, to the planning apparatus and considering all these material properties during optimization. In RayStation® this is achieved as material override. Other systems may have different names for the same functionality, for example density override, or CT override.

The method according to the invention may also be used for handling uncertainties in the placement of patient on the treatment support, such as the couch or chair, and/or other external equipment, such as fixation or bolus, which may have different materials and/or different thickness in different regions. The support is normally added to the image during planning, because the planning image was taken with the patient on another type of support. This is also done by material override, or corresponding functions depending on the planning system used. In some cases, synthetic CT data will be inserted in a CT image. Movement of the support, and/or of the patient on the couch will result in different material properties, which will affect any beam delivered through the support.

In the simplest embodiment, the material property may be electron density or mass density, depending on the type of radiation, where mass density is used for photons and electron density for electrons. There may also be other types of material property information, alone or in combination, for example, the atomic number Z or mass number A, ionization energy and mass density. For composite materials, this will include the material's atomic composition with relative fractions of the atomic numbers Z or mass numbers A, for the material, and/or the material's mean ionization energy and mass density. The robust optimization with respect to material property may be combined with conventional robust optimization with respect to patient geometry. The at least one parameter may also be related to a shape or position of the structure, where the material property function is used to set different scenarios for material property in the area of the structure based on different shapes or positions.

The invention also relates to a computer program product comprising computer readable code means which, when run in a computer will cause the computer to perform the method according to any of the embodiments disclosed in this document. The computer program product may be stored on a non-transitory memory device. The invention also relates to a computer system comprising a processor and a program memory, wherein the program memory includes such a computer program product to be executed in the processor.

In a specific embodiment the invention relates to a computer-based method for generating a radiotherapy treatment plan for a patient comprising the steps of
  obtaining an image of the patient and a desired dose to at least one portion of the patient
  identifying at least one structure in or adjacent the patient having unknown material properties,
  obtaining a set of different possible values for at least one material property,
  performing robust optimization with respect to the different possible values.

In a different embodiment, the invention relates to a computer-based method for generating a radiotherapy treatment plan for a patient comprising the steps of
  obtaining an image of the patient and a desired dose to at least one portion of the patient
  identifying at least one structure to be added to the image by changing the material settings, and having an unknown exact position relative to the patient,
  obtaining a set of different possible values for the position,
  performing robust optimization with respect to the different possible values.

In both cases, the robust optimization ensures that the resulting plan will have a sufficiently high quality for all the different possible material property values, or position values, respectively.

BRIEF DESCRIPTION OF DRAWINGS

The invention will be described in more detail in the following, by way of examples and with reference to the appended drawings.

DETAILED DESCRIPTION OF EMBODIMENTS

Figure 1:
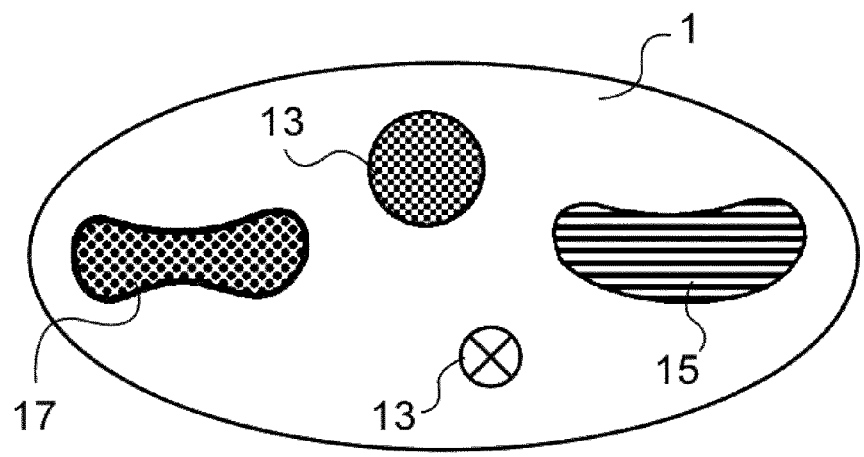
FIGS. 1 and 2 illustrate different situations in which the material properties of a region of the patient are not known.

FIG. 1 discloses a section through a medical image of a patient 11, including some internal organs 13, a hip 15 and a left hip prosthesis 17. As can be seen, any beam entering the patient 11 from the left will be affected by the prosthesis 17, and the material properties of the prosthesis will affect the dose, and or the positioning of the dose delivery within the patient. Different materials are used for implants and prosthetic devices, including a number of biocompatible metals and alloys. The different materials have different material properties, including density, which will affect the radiation differently and therefore should be considered in the treatment planning. If the material and its properties are not known, according to embodiments of the invention, a list of possible materials that are commonly used in such implants and their material property values of these different materials is obtained and the different material property values are used to define different scenarios for use in an optimization procedure arranged to perform robust optimization with respect to the different material property values.

Foreign materials may be found as implants in various parts of the body, and as teeth fillings. All of these will affect any radiation passing through them, in ways that will depend on the shape of the implant and the properties of the material, so there is a need to consider them in radiotherapy treatment planning for different parts of the body. The list of possible materials and their properties may be different for different types of prosthetics or implants. For hip replacements, for example, metals such as stainless steel, or titanium and alloys thereof are often used. In other applications, ceramics such as zirconia or calcium compositions, or polymers such as silicones or collagen are used. Teeth fillings may include a number of different materials including plastic, porcelain, dental amalgam, and gold.

Figure 2:
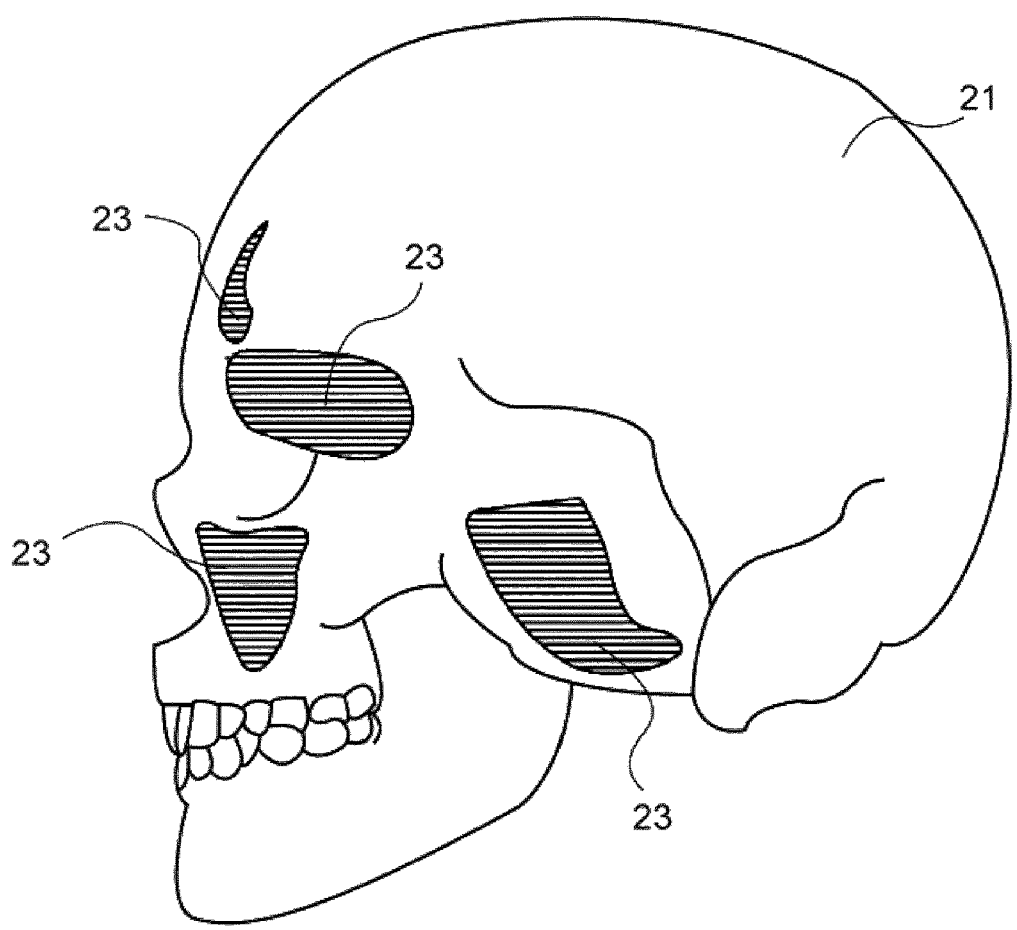

For some regions of the body the material properties may vary. FIG. 2 shows, as an example, a schematic drawing of a human head 21. The head has a number of nasal cavities 23, which may be filled with air and mucus in varying proportions, which will affect the radiation passing through the nasal cavities in different ways. To obtain a treatment plan that works both when the nasal cavities are mostly filled with air and when they are more or less filled with mucus, different material property values for air, mucus, and combinations of the two could be used in the robust planning.

Other regions of the body in which the material properties may vary include the thorax which may comprise more or less fluid, breasts, which may be more or less swollen, and the bowel, which may include gas pockets. For each of these, a set of possible material property values covering a range of different possible situations may be obtained and input to the optimization procedure.

Figure 3:
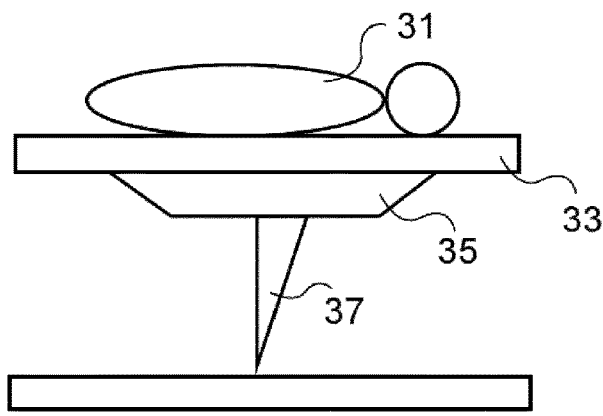
FIG. 3 illustrates a situation in which the exact position of a structure to be added to a medical image is not known.

FIG. 3 shows a patient 31 positioned on a couch 33 of a radiotherapy delivery system. As mentioned above, the CT image of the patient does not include the couch, and the couch used for imaging is usually different from the one used for treatment delivery. Therefore, the couch is added in the treatment planning procedure as a material override, or corresponding function, depending on the type of planning system used. The shape and material of the couch itself may be known, but there is usually an uncertainty in the position of the couch relative to the patient. As can be seen in FIG. 3, different portions of the couch have different shapes. For example, underneath the couch 33 there is a support structure 35 and a mechanism 37 for moving the couch. Different portions of the couch may also comprise different types of material. Therefore, different positions of the patient relative to the couch will affect any beam that passes through the couch differently. This can be handled by obtaining a definition of the couch itself to be added to the medical image of the patient as a material override, and setting a number of different possible positions for the couch in the material override information.

Other types of structures may also be added to a medical image instead of, or in addition to the couch. For example, the patient may instead be positioned on a chair or other type of support, and/or external equipment such as a bolus may be positioned in the path of the radiation. Fixation may also be applied to ensure that the patient has the right shape and is positioned, immobile, in the right place. For each of these, uncertainties in the relative position between the patient and the added structure may be handled by setting different positions for the added structure in a material override or corresponding function.

In some cases, the structures involved may also have an unknown shape, or the shape may change, which will also affect the treatment in ways that cannot be precisely known.

Figure 4:
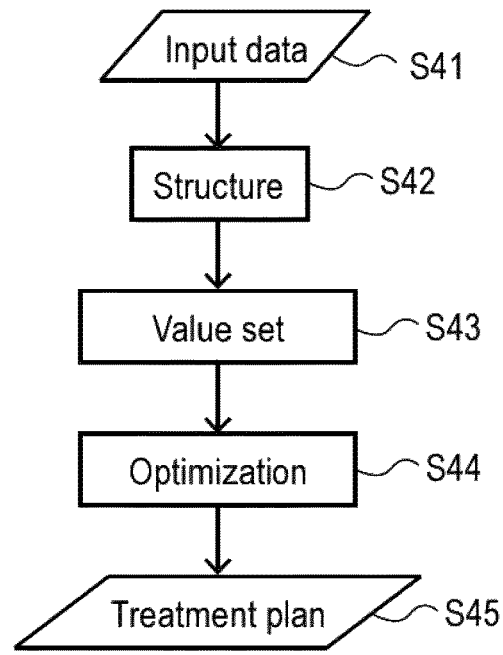
FIG. 4 is a flow chart of a method according to an embodiment of the invention

FIG. 4 is a flowchart of a method according to the invention. In a first step S41, input data to the process are provided. The input data include a medical image of the patient and a desired dose for at least a portion of the image, for example a tumor.

In step S42, a structure is identified, for which there is an uncertainty in one or more of material properties, position, and shape. There may be uncertainties in two or three of these factors for the same structure, and there may also be a case in which there is uncertainty in the position of one structure, in material properties for another structure and in the shape and material properties for a third structure. Of course, these are just examples; any combination of uncertainties may be present in one or more structures.

In step S43, a set of possible values for the structure is defined. In the case where the position and shape of the structure is known, such as the situation shown in FIGS. 1 and 2, such possible values will be related to the material properties, as discussed below. In other words, there will be at least a first and a second set of possible values for the material property or properties in question. In the case where the shape and material of the structure is known, such as the situation shown in FIG. 3, the possible values will be related to the position of the structure. In other words, there will be at least a first and a second possible position in the image in which the structure should be added, each corresponding to a possible relative position of the couch and the patient.

In step S44 an optimization is performed using an optimization problem taking into account the desired dose, and the set of possible values for the structure, in such a way that the result of the optimization will be a plan S45 that is sufficiently good for all possible values.

The material properties to be considered may be selected depending on the situation, for example, on the type of radiation used. For example, for proton or ion treatment more specific material property information may be desirable than for photon treatment. The material property values may be related to one or more of the following:
density/mass density
atomic composition with relative weights for different atoms
atomic number Z for the atoms
mass number A for the atoms
mean ionization energy As discussed in connection with FIG. 3, the uncertainty may also be in the positioning of a structure, in particular a structure to be added to the image. The uncertainty may also be in a shape of a structure, for example, in the case of tooth fillings, or gas bubbles in the intestines. One way of handling this in the image is by material override in the area where the structure should be positioned. According to embodiments of the invention, a number of different positions and/or shapes may be set as a set of values for material override and robust optimization may be performed with respect to these values.

As is common in robust planning, the different possible values in a set of possible values may be given different weights, depending on the likelihood that they will occur. For example, values indicating an overweight of air mixed with a certain amount of mucus in the sinuses may be considered to be the likeliest and therefore given the highest weights. Similarly, relative positions in which the patient is positioned near the center of the couch may be given the highest weights.

Figure 5:
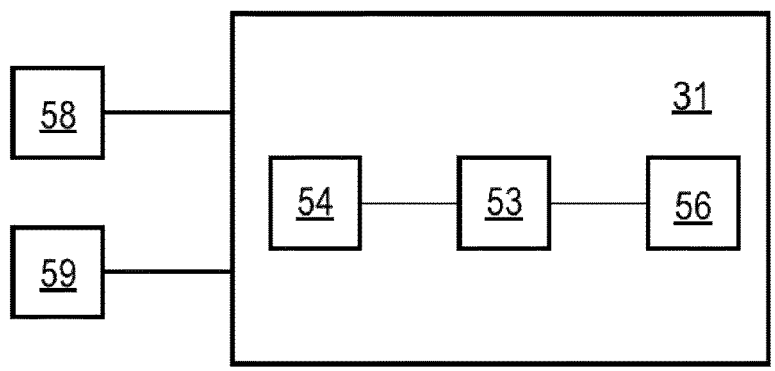
FIG. 5 is a schematic drawing of a computer system in which the inventive method may be implemented.

FIG. 5 is a schematic representation of a computer system in which the inventive treatment planning method may be performed. A computer 51 comprises a processor 53, a data memory 54 and a program memory 56. Preferably, one or more user input means 58, 59 are also present, in the form of a keyboard, a mouse, a joystick, voice recognition means or any other available user input means. The user input means may also be arranged to receive data from an external memory unit.

The data memory 54 comprises necessary data for performing the method, such as a desired dose distribution, and a segmented patient image. The program memory 56 holds a computer program arranged to make the computer perform the method steps according to some embodiment of the invention as outlined in FIG. 2.

As will be understood, the data memory 54 as well as the program memory 56 are shown and discussed schematically. There may be several data memory units, each holding one or more different types of data, or one data memory holding all data in a suitably structured way, and the same holds for the program memories. Both the program and the data can be found in one or more memories within the computer system or in another unit that is accessible from the computer system.

In the simplest embodiment, the material property may be electron density or mass density, depending on the type of radiation, where mass density is used for photons and electron density for electrons. There may also be other types of material property information, alone or in combination, for example, the atomic number Z or mass number A, ionization energy and mass density. For composite materials, this will include the material's atomic composition with relative fractions of the atomic numbers Z or mass numbers A, for the material, and the material's mean ionization energy and mass density. The robust optimization with respect to material property may be combined with conventional robust optimization with respect to patient geometry. The at least one parameter may also be related to a shape or position of the structure, where the material property function is used to set different scenarios for material property in the area of the structure based on different shapes or positions.

The invention claimed is:

1. A computer-based method of generating a radiotherapy treatment plan for a patient, comprising the following steps:
   obtaining an image of the patient and a desired dose to at least one portion of the patient;
   identifying at least one structure in the image for which there is an uncertainty in at least one parameter, wherein the structure includes at least one of: an implant or a prosthetic device, a part of the patient's body, such as a nasal cavity, or a structure external of the patient, such as a couch, a chair, a fixation or a bolus;
   defining two or more different scenarios for the structure, with respect to the at least one parameter, each scenario including a set of material override values for the structure, the values corresponding to different possible values for the at least one parameter; and
   performing calculations based on the at least two scenarios to provide robust evaluation data for each of the at least two scenarios and/or a robust optimized treatment plan with respect to all values in the set of material override values.

2. The method of claim 1, wherein the at least one parameter is related to the material properties of the structure and the set of material override values relate to at least one material property of the structure.

3. The method of claim 2, wherein the at least one material property of the structure includes a least one of density, atomic composition, atomic number or numbers A, mass number or numbers Z, and mean ionization energy for the material in the structure.

4. The method of claim 1, wherein the at least one structure is added to the image by changing the material settings in a portion of the image and the parameter is related to the position of the portion of the image, the method further comprising the steps of obtaining a definition of the structure.

5. The method of claim 1, wherein the at least one parameter is related to a shape of the structure.

6. The method of claim 1 comprising, if the calculation is performed to provide robust evaluation data, the step of using the robust evaluation data to evaluate the at least two scenarios.

7. The method of claim 1, comprising the step of assigning different weights to the different possible values in the calculation procedure.

8. A computer program product comprising a non-transitory computer readable storage medium having computer program code embodied therewith which, when run in a computer will cause the computer to perform the method of claim 1.

9. A computer system comprising a processor and a program memory, wherein the program memory includes a computer program code to perform the method of claim 1.

* * * * *